United States Patent [19]

Ishikawa et al.

[11] Patent Number: 4,582,924
[45] Date of Patent: Apr. 15, 1986

[54] α-FLUOROALKYL CARBOXYLIC ACID ESTERS AND PROCESS FOR PREPARING THE SAME

[75] Inventors: Nobuo Ishikawa; Takeshi Nakai, both of Yokohama, Japan

[73] Assignee: Daikin Kogyo Co., Ltd., Osaka, Japan

[21] Appl. No.: 586,946

[22] Filed: Mar. 7, 1984

[30] Foreign Application Priority Data

Mar. 9, 1983 [JP] Japan .................................. 58-38786
Mar. 9, 1983 [JP] Japan .................................. 58-38787

[51] Int. Cl.$^4$ .................... C07C 69/76; C07C 69/73; C07C 69/66
[52] U.S. Cl. ........................................ 560/57; 560/60; 560/183; 560/184; 560/174; 560/227; 562/586; 556/470
[58] Field of Search ................... 560/57, 60, 174, 227, 560/183, 184; 562/586

[56] References Cited

FOREIGN PATENT DOCUMENTS 2137712 2/1973 Fed. Rep. of Germany .
1455468 9/1966 France .

OTHER PUBLICATIONS

Purrington et al., "Prep of Esters Containing an α–CF$_3$ Group", in *Tetrahedron Letters*, vol. 25, No. 13, pp. 1329–1332, 1984.
Nakai et al., "Silyl Ketene Acetal Derived from Methyl β,β,β-Trifluoropropionate: A Versatile Reagent for Synthesis of α-Trifluoromethyl Carboxylic Esters", from Abstracts of 186th A.C.S. Meeting, D.C. 8/83, Fluo 24, Title and Contributor pages to *Tetrahedron Letters*, vol. 23, No. 10. pp. 1015, 1017.
Buxton et al., Journal of the Chemical Society, part 1, (1955), pp. 366–374.

*Primary Examiner*—Paul J. Killos
*Attorney, Agent, or Firm*—Armstrong, Nikaido, Marmelstein & Kubovcik

[57] ABSTRACT

An α-fluoroalkyl carboxylic acid ester of the general formula

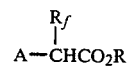

wherein A is $R^1R^2COR^3$— or $R^4CO$—, wherein $R^1$ and $R^2$ are independently hydrogen, alkyl, alkoxyl or phenyl, with or without the formation of a common ring therebetween, $R^3$ is hydrogen or alkyl, $R^4$ and R are independently alkyl, and $R_f$ is fluoroalkyl. The α-fluoroalkyl carboxylic acid ester is prepared by reacting a fluoroalkyl silyl ketene acetal of the formula

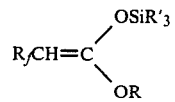

wherein R' is alkyl and $R_f$ and R are the same as defined above, with the corresponding acetal, ketone or acyl halide.

2 Claims, No Drawings

α-FLUOROALKYL CARBOXYLIC ACID ESTERS AND PROCESS FOR PREPARING THE SAME

BACKGROUND OF THE INVENTION

1. Field of the Invention

The present invention relates to α-fluoroalkyl carboxylic acid esters that are useful, for example, as an intermediate in the synthesis of physiologically active substances having a fluoroalkyl substituent and to a process for preparing the same.

2. Description of the Prior Art

A group of compounds having a $CF_3$ substituent have been noticed for their physiological activities. A possible general method of synthesis of such $CF_3$ containing compounds is to form various carbon-carbon bonds to a synthetic block having a $CF_3$ substituent. However, there are very few disclosures of such a method, for example, α-trifluoromethyl malonic acid ester published at the 8th Fluorine Chemistry Discussion in Japan (1982).

OBJECTS AND SUMMARY OF THE INVENTION

The present inventors thus noticed 3,3,3-trifluoropropionic acid esters (TFPE) as a such synthetic block and successfully synthesized their equivalent, namely, their ester enolate form or trifluoromethyl silyl ketene acetals in high yield. Further, starting from these compounds, these inventors succeeded in the synthesis of the corresponding fluorinated carboxylic acid esters, which has led to the present invention.

Accordingly it is an object of the present invention to provide α-fluoroalkylcarboxylic acid esters of the general formula

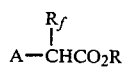

wherein A is selected from the group consisting of

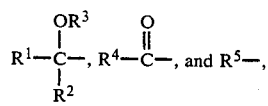

wherein $R^1$ and $R^2$ are independently a hydrogen atom, alkyl, phenyl, with or without the formation of a common ring therebetween, or alkoxy group, $R^3$ is a hydrogen atom or alkyl group, $R^4$ and $R^5$ are independently an alkyl group, R is an alkyl group, and $R_f$ is a fluoroalkyl group.

It is another object of the invention to provide a process for preparing the α-fluoroalkyl carboxlic acid esters, comprising reacting a fluoroalkyl silyl ketene acetal of the formula

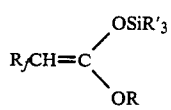

wherein R' is an alkyl group, and $R_f$ and R are respectively the same as defined above with a substrate selected from the group consisting of

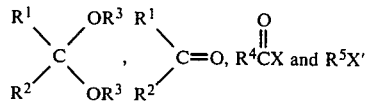

wherein $R^1$, $R^2$, $R^3$, $R^4$ and $R^5$ are respectively the same as defined above, and X and X' are independently a halogen atom.

In the present invention, $R_f$ in the above general formulas may be a fluoroalkyl group of 1 to 10 carbon atoms, for example, $-CF_3$, $-C_2F_5$, or $-C_3F_7$, and $R^3$ and R may be independently an alkyl group of 1 to 10 carbon atoms, for example, $-CH_3$, $-C_2H_5$, and $-C_3H_7$. Further, $R^1$ and $R^2$ may be independently an alkyl group of 1 to 10 carbon atoms as mentioned above, alkoxy group of 1 to 10 carbon atoms, for example, $-OCH_3$ and $-OC_2H_5$, or phenyl group. $R^1$ and $R^2$ can be changed properly according to the acetal or carbonyl compound used, and $R^1$ and $R^2$ may form a common ring. Further, $R^4$ and $R^5$ may be independently an alkyl group of 1 to 10 carbon atoms, for example, $-CH_3$, $-C_2H_5$, and $-C_3H_7$. X and X' may be independently a chlorine or bromine atom.

In the process of the present invention, the reaction is preferably conducted for 3 to 10 hours at $-85°$ to $-60°$ C. using an organic solvent, such as diethyl ether or dichloromethane. Other objects and advantages of the invention will become apparent from the following description of embodiments.

DESCRIPTION OF THE PREFERRED EMBODIMENTS

One of starting compounds of said silyl ketene acetal is a novel compound and which can be prepared, for example, by reacting trifluoropropionic acid ester 1 with trimethylsilyl triflate ($CF_3SO_2-$) as in the following reaction formula at a high yield.

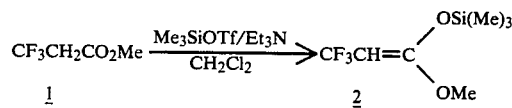

Such a high yield in the synthesis of silyl ketene acetal 2 is noteworthy since it has been known that if an ordinary ester having no $CF_3$ group is used as the starting material, the $Me_3SiOTf/Et_3N$ reaction system gives an α-trimethylsilyl ester. In fact, it has been even confirmed that methyl propionate, if used, gives the corresponding α-trimethylsilyl ester as the principal product. In contrast to that, it has been found that when an ester having a $CF_3$ group, which is highly electron attractive, at its α-position is used as the starting material as in the present invention, the reaction proceeds as mentioned above.

The chemical structure of acetal 2 was identified by $^1H$ NMR and $^{19}F$ NMR. It was confirmed that the ratio of geometric isomers was E:Z=1:4.

Further, from the finding that the acetal 2 as synthesized above can undergo the following reaction with various electrophilic reagents under Lewis acidic conditions, it has been revealed that this acetal can be used as a useful block for the synthesis of α-trifluoromethyl esters, etc.:

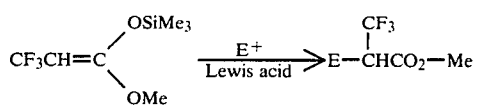

wherein E+ is an electrophilic reagent.

This reaction can be conducted with the reaction giving said acetal 2 in situ, namely, without isolation. For example, it has been found that an aldol addition type reaction, if applied to the acetal 2, gives α-trifluoromethyl carboxylic acid ester 4 according to the following reaction formula:

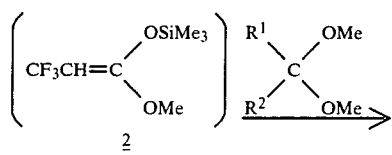

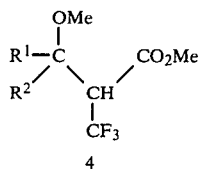

More specifically, when an aldol additive type reaction was performed with acetals using trimethylsilyl triflate (Me₃SiOTf) as catalyst as in the above reaction, 1.2 equivalent of Me₃SiOTf was used relative to the ester 1 in consideration of the fact that the acetal 2 releases fluoride ions F⁻ readily. The acetal 2 produced was cooled down to −78° C. in situ and then various substrates were added thereto for the addition reaction. The reaction was completed within several hours giving the corresponding aldol adduct 4 in high yield. Aldol adduct compounds thus produced are listed in Table 1. Except for one example in the case of sample 4, the reaction always showed only a low diastereo selectivity.

TABLE 1

| Sample | Electrophile | Reaction condition | Product | Yield, % (diastereo selection ratio) |
|---|---|---|---|---|
| 1 | CH₃\C(OMe)₂/CH₃ | −78° C. 6 h | MeO\C(CH₃)(H₃C)—CH(CF₃)\CO₂Me | 74 |
| 2 | CH₃—CH(OMe)₂ | −78° C. 6 h | MeO\H₃C—CH—CH(CF₃)\CO₂Me | 81 (55:45) |
| 3 | PhCH(OMe)₂ | −78° C. 4.5 h | Ph—CH(OMe)—CH(CF₃)—CO₂Me | 89 (67:33) |
| 4 | (CH₃)₃C-cyclohexyl-C(OMe)₂ | −78° C. 9 h | (CH₃)₃C-cyclohexyl-C(OMe)(CH—CO₂Me) | 82 (100:0) |
| 5 | PhCH=CH—CH(OMe)₂ | −78° C. 5 h | PhCH=CH—CH—CH(CF₃)—CO₂Me | 92 (55:45) |
| 6 | HC(OMe)₃ | −78° C. 5 h | MeO—CH(OMe)—CH(CF₃)—CO₂Me | 76 |

TABLE 1-continued

| Sample | Electrophile | Reaction condition | Product | Yield, % (diastereo selection ratio) |
|---|---|---|---|---|
| 7 | PhCHO | −78° C. 5 h | PhCH(OH)CH(CF₃)CO₂Me | 93 (60:40) |

It is noted that the erythro form of the above sample 5 is equivalent to the trifluoro form of an intermediate used for the synthesis of antibiotics oudemansin. It is thus expected that trifluorooudemansin can be synthesized by the following reaction:

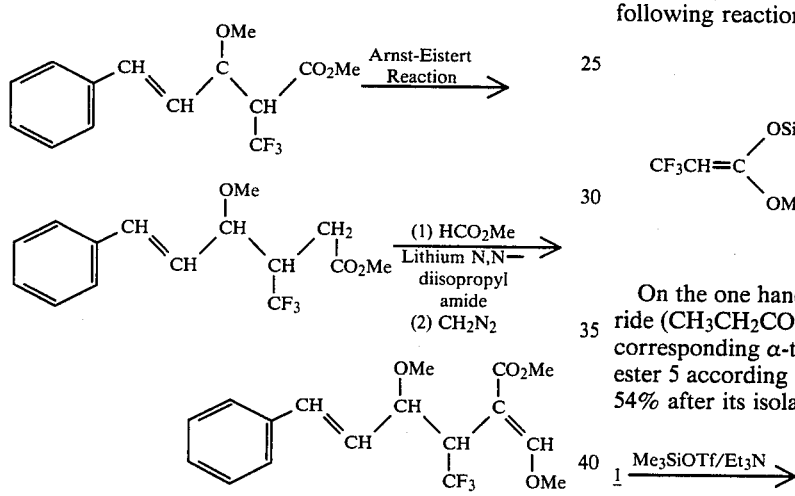

It has been confirmed that, as in the above case of Sample 7, the aldol addition reaction of acetal 2 and benzaldehyde gives the corresponding β-hydroxy-α-trifluoromethyl ester in high yield.

On the other hand, it is conceivable to convert the aldol adduct 4 to β-hydroxycarboxylic acid ester through substitution of an alkoxy group for the hydroxyl group at the β-position under presence of phenylthiotrimethylsilane and zinc iodide or to α,β-unsaturated carboxylic acid ester at an acidic condition, for example, under presence of acidic alumina according to the following reaction:

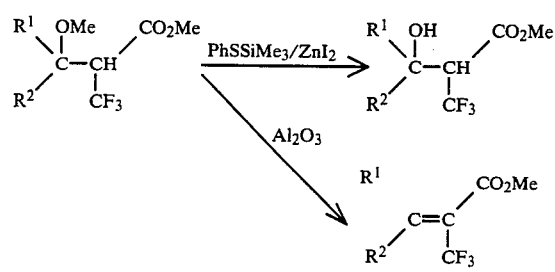

The above acetal 2 can also be reacted with a carbonyl compound

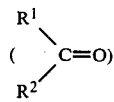

for conversion to the corresponding α-trifluoromethyl-β-hydroxycarboxylic acid ester 4' according to the following reaction:

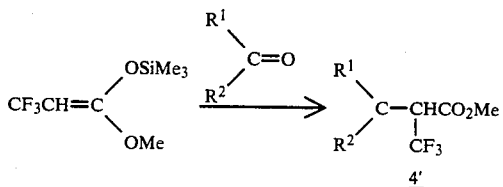

On the one hand, when reacted with propionyl chloride (CH₃CH₂COCl), the acetal 2 was converted to the corresponding α-trifluoromethyl-β-ketocarboxylic acid ester 5 according to the following reaction in a yield of 54% after its isolation:

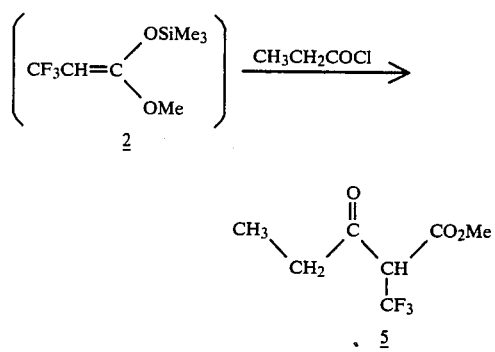

It was noted however that the isolated acetal 2, when dissolved in methylene chloride, did not react with propionyl chloride and even with further addition of triethylamine to this reaction system there was observed no reaction in this system either.

Next, alkylation of the above acetal 2 was investigated. Since Lewis acid/zinc bromide was found effective in the alkylation of this compound, an active alkyl halide chloromethyl ethyl ether was reacted with the acetal 2 under presence of a catalytic amount of zinc bromide, when the corresponding alkylated compound 6 was produced according to the following reaction:

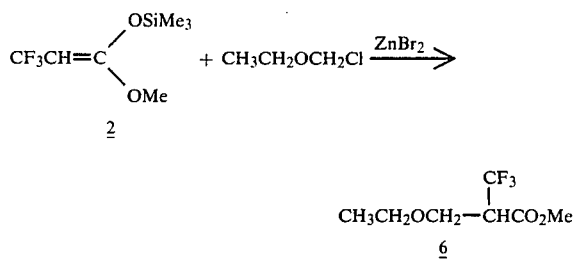

$$\underset{2}{\text{CF}_3\text{CH}=\text{C}\begin{array}{c}\text{OSiMe}_3\\ \\ \text{OMe}\end{array}} + \text{CH}_3\text{CH}_2\text{OCH}_2\text{Cl} \xrightarrow{\text{ZnBr}_2}$$

$$\underset{6}{\text{CH}_3\text{CH}_2\text{OCH}_2-\overset{\overset{\text{CF}_3}{|}}{\text{CH}}\text{CO}_2\text{Me}}$$

The above alkylated compound 6 was produced at a yield of 67% from TPFE and at a yield of 85% from the acetal 2. The alkyl halide used in the above reaction is not limited to chloromethyl ethyl ether. Namely, other active alkyl halides can be used for it.

The invention will be more clearly understood with reference to the following Examples:

EXAMPLE 1

Synthesis of TFPE

Methyl 2-(trifluoromethyl)-3,3,3-trifluoropropionate. To 232 g (1.0 mol) of octafluoroisobutene-methanol adduct, 200 ml of conc. sulfuric acid was added dropwise and the solution was agitated overnight at room temperature. It was then poured over ice. The oily layer was separated, washed with water, saturated sodium bicarbonate solution, and water successively, and then dried on magnesium sulfate. Purification by distillation gave methyl 2-(trifluoromethyl)-3,3,3-trifluoropropionate (184 g, 88%). Its analysis gave the following data:

B.p.: 89°–90° C.

$^{19}$F NMR (neat): $-12.5$ (d, J=6.2 Hz).

Methyl 3,3,3-trifluoropropionate (TFPE). To a solution of 105 g (0.5 mol) of methyl 2-(trifluoromethyl)-3,3,3-trifluoropropionate in 250 ml of water, a solution of 150 g (1.5 mol) of potassium acetate in 500 ml of water was added dropwise and the mixture was refluxed for 5 hours. After separation of the oily layer, extraction was made from the water layer that was left using methylene chloride. The oily layer and extracted fraction were joined and dried. After evaporation of methylene chloride under atmospheric pressure, purification by distillation was performed to give methyl 3,3,3-trifluoropropionate (TFPE) (54.07 g, 76%). Its analysis gave the following data:

B.p.: 95°–95.5° C.

IR (capillary film): 2970, 1760, 1440, 1230, 1120 cm$^{-1}$.

$^1$H NMR (CCl$_4$): 3.13 (q, J=10.3 Hz, 2H). 3.77 (s, 3H) $^{19}$F NMR (neat): $-12.7$ (t, J=10.3 Hz).

Synthesis of trifluoromethylsilylketene acetal:

1-(Trimethylsiloxy)-1-methoxy-3,3,3-trifluoro-1-propene (E:Z=1:4). To a mixture of 1.00 ml (5.5 mmol) of trimethylsilyl triflate, 0.77 ml (5.5 mmol) of triethylamine and 3 ml of dry methylene chloride, a solution of 0.71 g (5 mmol) of TFPE as above prepared in 3 ml of methylene chloride was added dropwise and the mixture was agitated for 18 hours at room temperature. After attaching a trap of $-90°$ C., flash evaporation was performed at a condition of room temperature/2 mmHg. 1-(trimethylsiloxy)-1-methoxy-3,3,3-trifluoro-1-propene was thus produced (yield: 86%). Its analysis gave the following data:

E form:

$^1$H-NMR (CDCl$_3$): δ0.32 (s,9H), 3.67 (s,3H), 3.90 (q, J=7.6 Hz, 1H).

$^{19}$F-NMR (CDCl$_3$): δ-23.9 (d, J=7.6 Hz).

Z form:

$^1$H-NMR (CDCl$_3$): δ0.24 (s, 9H), 3.61 (s,3H), 3.96 (q, J=7.1 Hz, 1H).

$^{19}$F-NMR (CDCl$_3$): δ-24.2 (d, J=7.1 Hz).

It is noted that the yield was estimated from $^{19}$F NMR data using fluorobenzene as the standard and the ratio E/Z was also estimated from $^{19}$F NMR data.

Synthesis of α-trifluoromethyl-β-methoxycarboxylic acid ester: With the above acetal in situ, the reaction mixture was cooled down to $-78°$ C. and an acetal of a general formula $$\left[\begin{array}{c}\text{CH}_3\\ \diagdown\\ \diagup\\ \text{CH}_3\end{array}\text{C}\begin{array}{c}\text{OMe}\\ \diagup\\ \diagdown\\ \text{OMe}\end{array}\right]$$

was added thereto. 6 hour reaction under presence of Me$_3$SiOTf as catalyst gave the target compound α-trifluoromethyl-β-methoxy-β-methylbutanoic acid ester of the following formula at a yield of 74%:

$$\left[\begin{array}{c}\text{Me}\\ \diagdown\\ \diagup\\ \text{Me}\end{array}\overset{\overset{\text{OMe}}{|}}{\text{C}}-\text{CH}-\text{CO}_2\text{Me}\\ \phantom{xxxxx}|\\ \phantom{xxxxx}\text{CF}_3\right]$$

EXAMPLE 2

Synthesis of α-trifluoromethyl-β-ketocarboxylic acid ester: The ketene acetal as prepared in Example 1 was reacted with acid chloride CH$_3$CH$_2$COCl. The corresponding α-trifluoromethyl-β-ketopentanoic acid ester was thus produced in a yield of 53%.

EXAMPLE 3

Synthesis of another α-trifluoromethyl-β-ketocarboxylic acid ester: The above acetal was also reacted with CH$_3$(CH$_2$)$_3$COCl. The corresponding ester was produced in a yield of 58%.

EXAMPLE 4

Synthesis of α-trifluoromethyl-β-ethoxycarboxylic acid ester: The above acetal was reacted with chloromethyl ethyl ether under presence of a catalytic amount of zinc bromide. When this reaction was performed with the acetal produced in situ, there was a low yield of 40%. However, when the acetal produced was flash evaporated for separation of the quarternary ammonium salt derived from triethylamine and then subjected to the same reaction, the corresponding α-trifluoromethyl-β-ethoxycarboxylic acid ester in its halide form was produced in a high yield (85% from the acetal).

Obviously, other modifications and variations of the present invention are possible in light of the above techniques and it is to be understood that changes may be made in the specific embodiments described without departing from the scope of the invention as defined by the appended claims.

What is claimed is:

1. An α-fluoroalkyl carboxylic acid ester of the formula

wherein A is

wherein $R^1$ is hydrogen, alkyl of 1–10 carbon atoms, alkoxyl of 1–10 carbon atoms or phenyl, $R^2$ is alkyl of 1–10 carbon atoms, alkoxyl of 1–10 carbon atoms or phenyl, with or without formation of a common ring between $R^1$ and $R^2$; $R^3$ is hydrogen or alkyl of 1–10 carbon atoms, $R^4$ is alkyl of 1–10 carbon atoms; R is alkyl of 1–10 carbon atoms and $R_f$ is fluoroalkyl of 1–10 carbon atoms.

2. A process for preparing an α-fluoroalkyl carboxylic acid of the formula

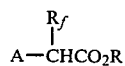

wherein A is

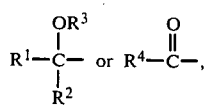

wherein $R^1$ and $R^2$ are independently hydrogen, alkyl of 1–10 carbon atoms, alkoxyl of 1–10 carbon atoms or phenyl, with or without the formation of a common ring therebetween; $R^3$ is hydrogen or alkyl of 1–10 carbon atoms; $R^4$ is alkyl of 1–10 carbon atoms; R is alkyl of 1–10 carbon atoms and $R_f$ is fluoroalkyl of 1–10 carbon atoms, comprising reacting (1) a fluoroalkyl silyl ketene acetal of the formula

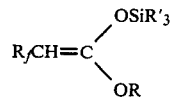

wherein $R_f$ and R are as defined above and R' is alkyl of 1–10 carbon atoms, with (2) a substrate selected from the group consisting of

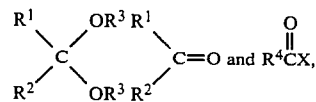

wherein $R^1$, $R^2$, $R^3$ and $R^4$ are as defined above and X is halogen.

* * * * *